United States Patent [19]

Mehler

[11] Patent Number: 4,956,993

[45] Date of Patent: Sep. 18, 1990

[54] SOIL INFILTROMETER

[75] Inventor: Marvin R. Mehler, Hutsonville, Ill.

[73] Assignee: Marathon Oil Company, Findlay, Ohio

[21] Appl. No.: 343,101

[22] Filed: Apr. 25, 1989

[51] Int. Cl.$^5$ ............................................. G01N 15/08
[52] U.S. Cl. ........................................................ 73/38
[58] Field of Search .................................... 73/38, 73

[56] References Cited

U.S. PATENT DOCUMENTS

| 2,540,096 | 2/1951 | Bull | 73/38 |
|---|---|---|---|
| 2,913,897 | 11/1959 | Kirkham et al. | 73/38 |
| 2,923,148 | 2/1960 | Kirkham et al. | 73/86 |
| 2,949,766 | 7/1960 | Kirkham et al. | 73/38 |
| 3,861,196 | 1/1975 | Domenighetti | 73/38 |
| 4,164,139 | 7/1979 | Jones | 73/38 |
| 4,478,069 | 10/1984 | Zuckerwar | 73/38 |

FOREIGN PATENT DOCUMENTS

| 2576414 | 7/1986 | France | 73/38 |
|---|---|---|---|
| 2576415 | 7/1986 | France . | |
| 129934 | 2/1978 | German Democratic Rep. | 73/38 |
| 543851 | 5/1977 | U.S.S.R. | 73/38 |
| 1158902 | 5/1985 | U.S.S.R. | 73/38 |
| 1257468 | 7/1986 | U.S.S.R. | 73/38 |

Primary Examiner—John Chapman
Assistant Examiner—Joseph W. Roskos
Attorney, Agent, or Firm—Jack L. Hummel; Jack E. Ebel

[57] ABSTRACT

A soil infiltrometer for making permeability measurements in the field. A small reservoir is concentrically placed inside a large reservoir and both are filled with water. The small reservoir consists of a relatively large base receptacle and an upwardly extending tube. Because the small reservoir has a much smaller volume than the large reservoir the effects of thermal expansion and temperature changes are minimized, and the accuracy of determining the quantity of water lost to the soil is increased. A sight level gauge permits the permeation of water from the small reservoir to be noted.

18 Claims, 4 Drawing Sheets

SOIL INFILTROMETER

Field of the Invention

This invention relates to a method and means useful in determining the permeability of soil. More particularly, it relates to a soil infiltrometer designed for use in the field.

Background of the Invention

The determination of soil permeability is routinely required for most construction projects, and over the years a large number of different methods and test equipment have been designed to obtain the necessary data. For some purposes core samples are taken and analyzed in the laboratory. For other purposes field measurements are preferred. For example, many different types of devices have been designed for on-site measurement of the permeability of roadbeds and bituminous roadway surfaces by determining the flow of liquid or gas through the relatively thin surface in question.

With the increasing importance placed on the ecological effects of leakage from waste storage pits, it has become important to be able to predict the volume of liquid which would flow from the storage pit over a period of time. Because the liner of a waste storage pit generally consists of compacted soil, it is not practical to take core samples for subsequent analysis in the laboratory. Infiltration data must instead be taken on site. The devices available for on-site testing, however, are generally not suitable for measuring flow through large areas of the relatively thick lining of a waste pit with the necessary accuracy. Although the thickness of the compacted soil of the lining will vary depending upon the materials involved, the thickness in any event can be substantial, in the order of 1½ feet or more.

What is needed is a relatively simple device which can be set up and operated in the field, which is large enough to test a relatively large lining area, yet is highly accurate, enabling small volumes of water lost through the soil to be measured. It should also take into account the boundary effects of liquid flow as well as the effects of temperature and thermal expansion.

A known method of reducing the boundary effects of water flowing into a layer of interest from a test reservoir is to employ a concentric ring method of measurement. In such an arrangement a small circular ring or cylinder is placed on the layer within a larger ring or cylinder. The space within the small ring comprises an inner chamber, which functions as the test chamber, and the annulus between the inner and outer rings comprises an outer chamber. Both chambers are filled with water and the amount of water lost from the inner chamber is measured. The flow of water from the outer chamber down into the layer acts as a barrier to radially outward flow of water from the inner chamber, effectively nullifying the tendency of the outer boundary of soil surrounding the soil directly beneath the test chamber to absorb water from the test chamber.

While such an arrangement is preferred in order to minimize the boundary effect of water leakage, such devices normally require a mechanism including float valves and a recorder for measuring the volume of water leaking into the soil over a period of time. This would be overly sophisticated for the type of field usage contemplated in the measurement of waste storage pit linings. Moreover, known devices of this type are not as accurate as desired because they do not compensate for the effects of temperature and thermal expansion. A simpler but more accurate soil infiltrometer designed for field use is needed.

Summary of the Invention

In accordance with the invention a soil infiltrometer is provided which comprises a large reservoir having an open bottom resting on the soil and a small reservoir within the large reservoir, also having an open bottom resting on the soil. The small reservoir is spaced from the periphery of the large reservoir and is sealed from the large reservoir. The small reservoir comprises a relatively large receptacle adjacent the soil and a relatively small receptacle extending upwardly therefrom. The reservoirs are constructed so that the volume of the large reservoir greatly exceeds the volume of the small reservoir. The small volume of the inner reservoir minimizes the effects of thermal expansion while the large volume of the outer reservoir minimizes temperature changes and ensures that the height of the water column changes very slowly as water permeates the boundary area of the test liner. In addition, the reservoirs are arranged so that the ratio of the top surface area of the water in the large reservoir to the upper surface area of the soil covered by the large reservoir greatly exceeds the ratio of the top surface area of the water in the small reservoir to the soil covered by the small reservoir. The net effect of this design on the large outer reservoir is to maintain a narrow range of water levels for a large range of water quantities. The net effect of the design on the small inner reservoir is to produce a large deviation in water level for a small loss of water, which facilitates accurate measurement.

Preferably, the reservoirs are circular in transverse cross section and means are provided for preventing evaporation losses. Simple but very effective means consistent with useage in a field device are provided for maintaining the water in the reservoirs at the same level.

These and other aspects of the invention, as well as other benefits thereof, will readily be ascertained from the more detailed description of the preferred embodiment of the invention which follows.

Description of the Preferred Embodiment

Figure 1:
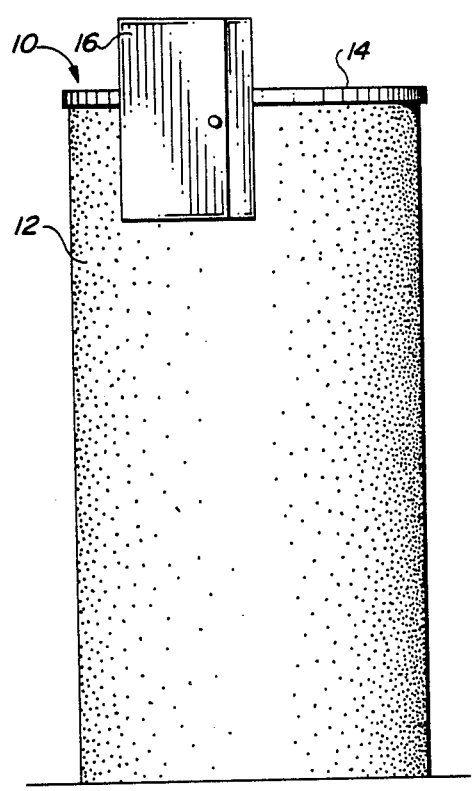
FIG. 1 is a pictorial view of the assembled infiltrometer of the present invention.

Referring to FIG. 1, the soil infiltrometer 10 of the present invention is comprised of a relatively tall outer cylinder 12 the top of which may be covered by a lid or roof 14 and the open bottom of which is resting on the ground. A level control panel 16, the details of which are described below, is secured to the upper portion of the cylinder 12. The cylinder is preferably of substantial size so that the water level in the cylinder does not drop rapidly due to permeation into the soil. For example, the inner diameter of the cylinder may be 6 feet while the height may be about 12 feet.

Figure 2:
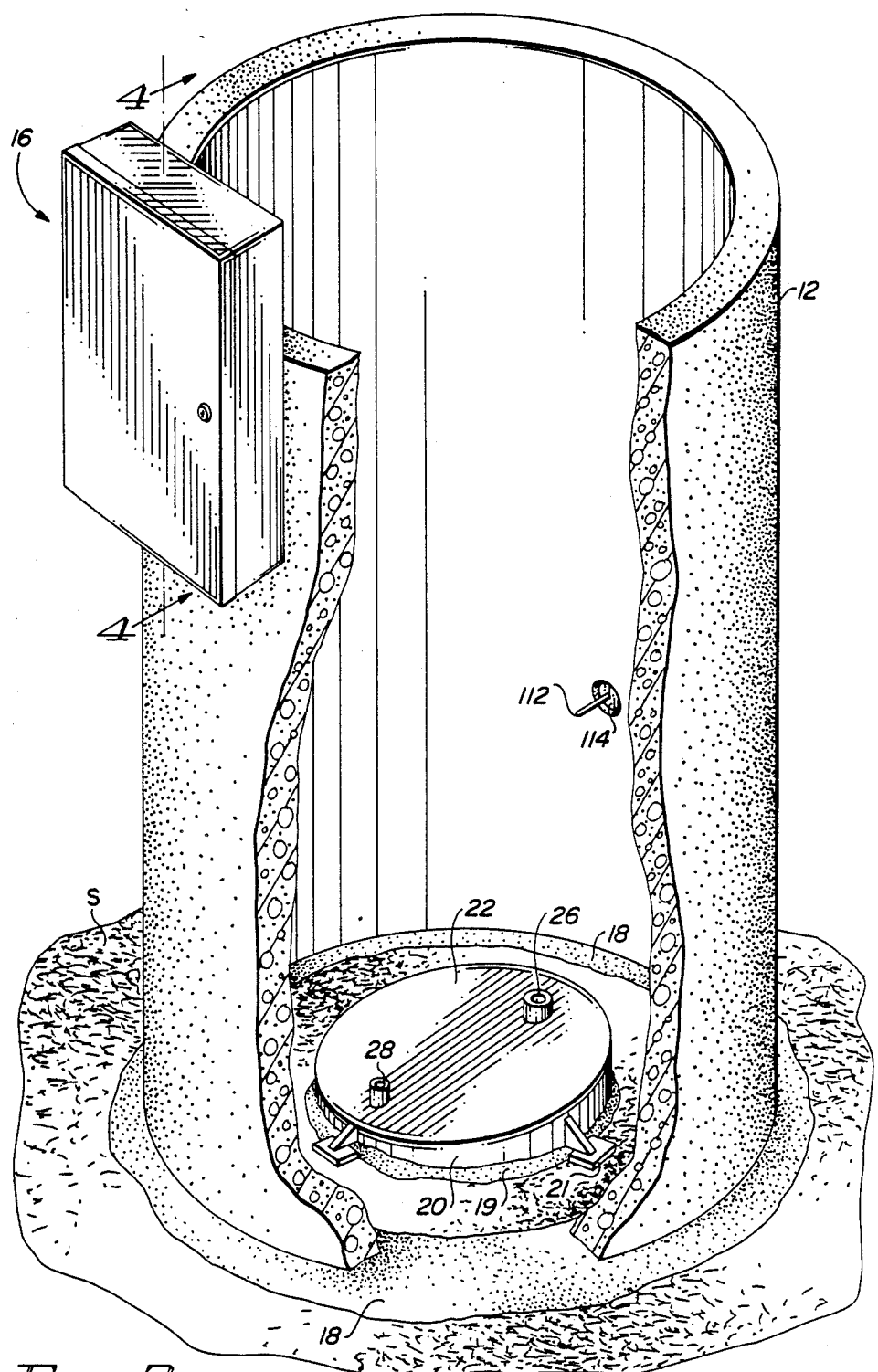
FIG. 2 is a pictorial view, shown partially in section, of the infiltrometer of FIG. 1.
Figure 3:
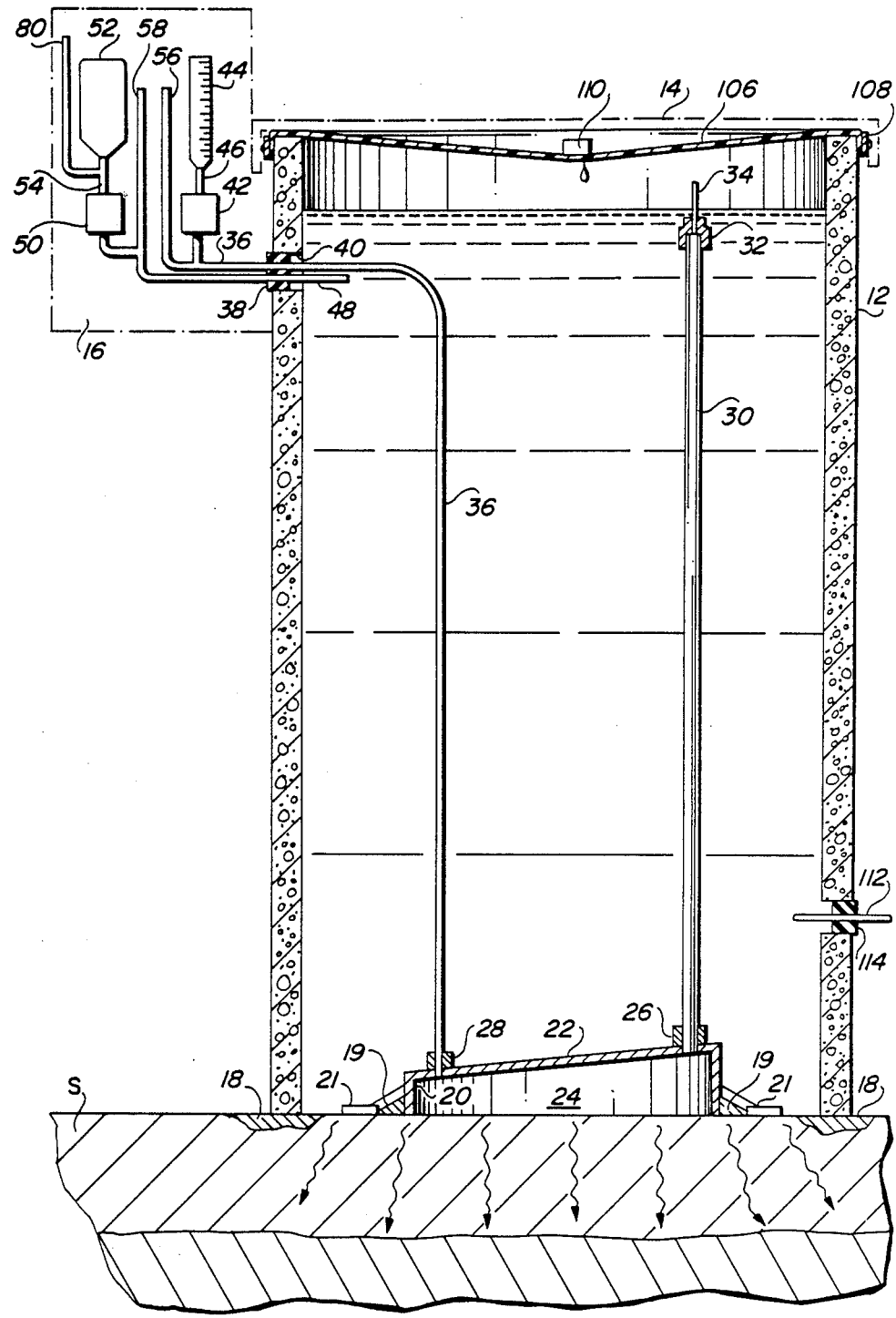
FIG. 3 is a longitudinal sectional view of the infiltrometer of FIG. 2, with the liquid level control means being schematically shown.

Referring to FIGS. 2 and 3, the cylinder 12, illustrated as being formed from concrete, is shown with its bottom supported on compacted soil S which has been treated in the area of the cylinder bottom with a sealant 18 such as a mixture of bentonite and clay prior to the cylinder being set in place. The bentonite will hydrate and swell upon contact with water, thus effectively sealing all the voids between the cylinder and the soil surface. A much smaller cylinder 20, illustrated as being fabricated from metal, which also has an open bottom is positioned within the outer cylinder 12 on the compacted soil S. Instead of applying sealant to the area of the compacted soil directly beneath the wall of the small cylinder 20 a heavy fillet of sealing material 18 is applied between the outside of the cylinder 20 and the soil. This ensures a good seal without contaminating the test surface inside the small cylinder. The upper end of the cylinder 20 is sealed with a lid or cover 22 to form a test chamber 24 within the cylinder 20. The cover 22 should be massive in order to weight the cylinder 20 down against the soil, thus ensuring a good seal with the soil. The massive cover also serves to resist the torque created by the installation of the riser pipe 30, described below. Pads 21 may be attached to the cylinder 20 at spaced intervals around the circumference so as to provide additional support surface to minimize any tendency of the cylinder 20 to sink into the mud during operation.

The upper end of the cylinder 20 is slightly angled to cause the cover 22 to be sloped, thus creating a pocket in the test chamber 24 that is higher than the rest of the chamber to facilitate the escape of air during filling of the cylinders in a manner to be described. The diameter of the cylinder 20 preferably is about half the diameter of the cylinder 12 and the height of the cylinder 20 is a great deal shorter than the height of the cylinder 12. For example, with an outer cylinder of about 12 feet in height the inner cylinder may be only about 6 inches high at its highest point. As illustrated, the cylinders are concentrically arranged.

Extending upwardly from the upper portion of the cover 22 is a threaded coupling 26 having a relatively large inside diameter, such as about 1½ inches. Extending upwardly from the lower portion of the cover 22 is a threaded coupling 28 having a smaller inside diameter, such as about ½ inch. A riser pipe 30 extends upwardly from the coupling 26 to a point below the surface of the water in the cylinder 12, and a bushing 32 connects the pipe 30 to a short length of copper tubing 34 extending above the level of the water. A length of copper tubing 36 extends upwardly from the coupling 28 and through a conduit in a rubber stopper 38 plugging an opening 40 in the wall of the cylinder 12.

The tubing 36 extends outside the cylinder 12 into a level chamber 42 associated with a graduated cylinder 44. A length of tubing 46 connects the interior of the cylinder 44 to the interior of the level chamber 42. In addition, a length of copper tubing 48 extends from a point within the cylinder 12 in the vicinity of the stopper 40, through a second conduit in the stopper and into a level chamber 50 associated with a water container 52. A length of tubing 54 connects the interior of the container 52 to the interior of the level chamber 50. Glass tubes 56 and 58, connected to tubing 36 and 48, respectively, enable the water levels in the inner and outer reservoirs to be viewed.

The interiors of the small cylinder 20, the riser pipe 30, the tube 36 and the level chamber 42 make up the total volume comprising the small reservoir. The interiors of the large cylinder 12, the tubing 48 and the level chamber 50 less the volume taken up by the cylinder 20, the pipe 30, and the tubing 36 and 48 make up the volume of a large reservoir. It can be seen that the volume of the large reservoir is much greater than the volume of the small reservoir.

Figure 4:
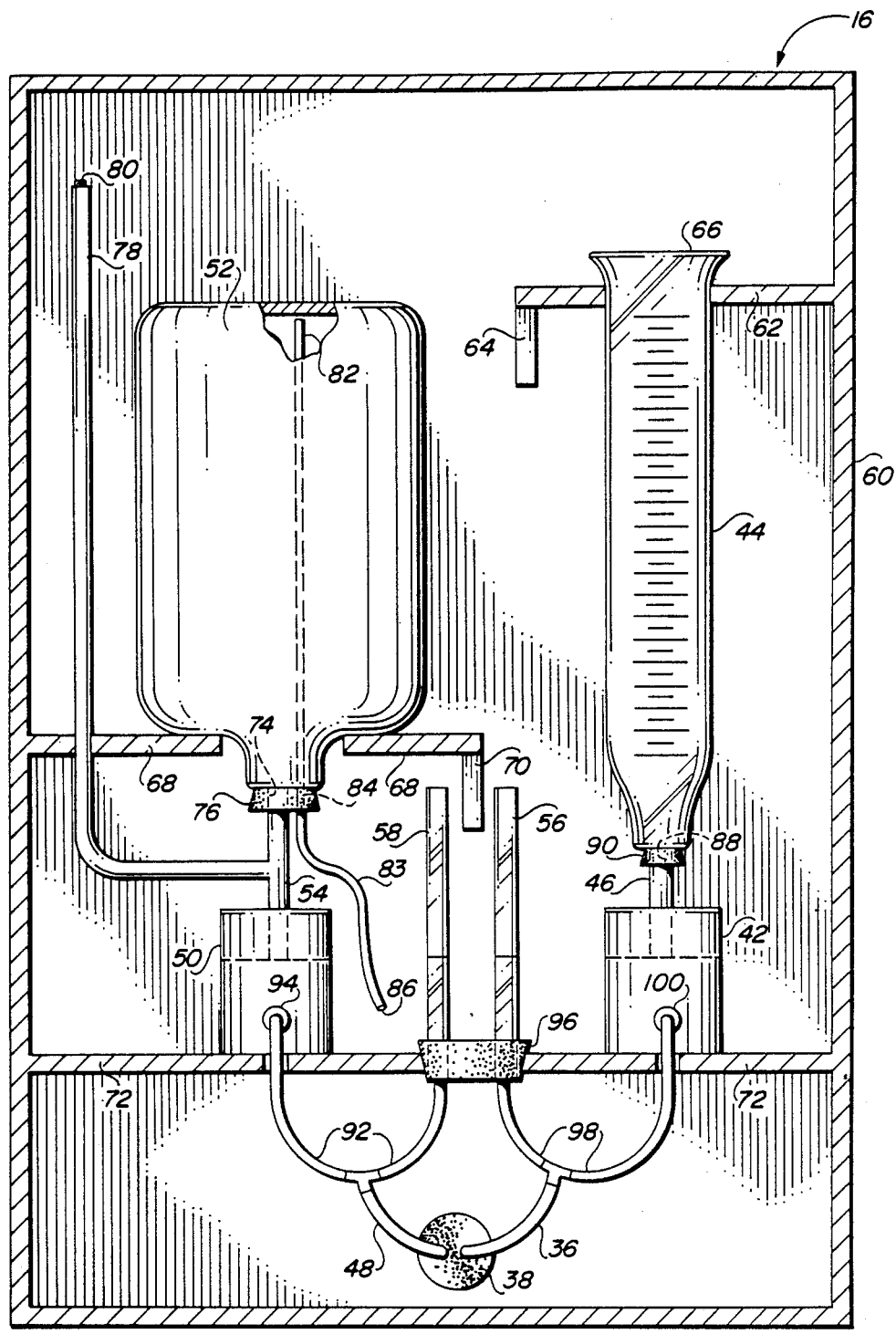
FIG. 4 is an enlarged sectional view of the liquid level control panel taken along line 4—4 of FIG. 2, showing the liquid level control means utilized in the infiltrometer.

Referring to FIG. 4, the level control panel 16 comprises a frame 60 which is mounted to the exterior of the cylinder 12 by any suitable means. Although specific mounting means are not shown in the drawings, it will be appreciated that suitable support beams can be bolted to the cylinder and the frame 60 can be attached to the beams. Other suitable support surfaces can be attached to the frame 60 by bolts or screws. Thus, a horizontal support or plate 62, which may be attached to a side wall of the frame 60 and to a vertical support 64 connected to the frame, contains an aperture through which the cylinder 44 extends. The horizontal support surface adjacent the aperture in the plate 62 supports the flange 66 of the inverted graduated cylinder 44. Similarly, the jug or container 52 is supported by horizontal support 68 which is attached to the other side wall of the frame 60 and to the vertical support 70. The neck of the container 52 extends through an aperture in the horizontal support 68. Another horizontal support 72 extends from one side wall of the frame to the other and supports the level chambers 42 and 50.

Still referring to FIG. 4, the tube 54 connecting the container 52 to the level chamber 50 is connected to the interior of the container 52 through a conduit 74 in stopper 76. The tube 54 must be of sufficient diameter, typically greater than ½ inch, to allow self-sustaining flow as discussed in more detail hereinafter. The tube 54 terminates in the interior of the chamber 50 at the surface of the water in the chamber 50. It is further connected to a fill tube 78 which extends through an aperture in the support 68 and terminates at a point higher than the top of the container 52. A cork or other stopper 80 normally seals the end of the tube 78. A small diameter rigid tube 82, preferably comprised of glass, extends through a second conduit 84 in the stopper 76 to a point in the interior of the container 52 adjacent the top of the container. Flexible tubing 83 extends from tube 82 to a convenient location where the end of the tubing is sealed by a cork or other stopper 86.

The tube 46, also of sufficient diameter to support self-sustaining flow, extends through a conduit 88 in the stopper 90 in the mouth of the graduated cylinder 44. The lower end of the tube 46 terminates at the surface of the water in the level chamber 42. The chamber 50 is connected by tubing 92 which extends from an aperture in stopper 94 to an aperture in the stopper 96 in the horizontal support 72. The glass sight tube 58 is connected to the tubing 92 through the stopper 96. The tubing 92 is connected as by a Y-connection to the tubing 48. In the same manner tubing 98 connects the sight tube 56 through a second aperture in stopper 96 to an aperture in the stopper 100 in the level chamber 42. The tubing 98 is connected as by a Y-connection to the tubing 36.

To install the equipment, as shown in FIG. 2 the test chamber consisting of the small cylinder 20 and cover 22 is set on the compacted soil S without gouging or otherwise disturbing the soil. A seal 18 is then applied around the outside of the cylinder 20 as described above. The outer cylinder 12 is then set in place on the outer ring of sealer so that it is centered about the test chamber, again taking care not to disturb the sealer or the soil. As previously stated, typical dimensions of the outer cylinder 14 would be 12 feet high and 6 feet in diameter. The test chamber would then typically be about 6 inches high at the highest point of the cylinder 20 and 3 feet in diameter.

Referring to FIG. 3, the copper tubing 36 is connected to the coupling 28 and inserted through stopper 38. The tubing 48 may be inserted through the stopper 38 at the same time. Then, with the riser pipe 30 resting on the top of the coupling 26 but not yet threaded into it, thereby allowing water to flow through the coupling, water is introduced through the open top of the outer cylinder 12. The water not only fills the large reservoir but also the small reservoir by flowing through the coupling 26 into the interior of the cylinder 20. Water is added until the desired level is reached, at which time the top of the riser pipe 30 will be a few inches below the water level. The riser pipe can then be threaded into place in the coupling 26. In this way the inner cylinder is filled at the same time as the outer cylinder, thus preventing the sealer from being blown out by the unequal pressures which would result from filling each cylinder separately. After the pipe 30 has been screwed into place the tubing 34 is connected by bushing 32. By making the tubing 34 long enough to extend above the surface of the water the two chambers or reservoirs are effectively isolated from each other.

Figure 6:
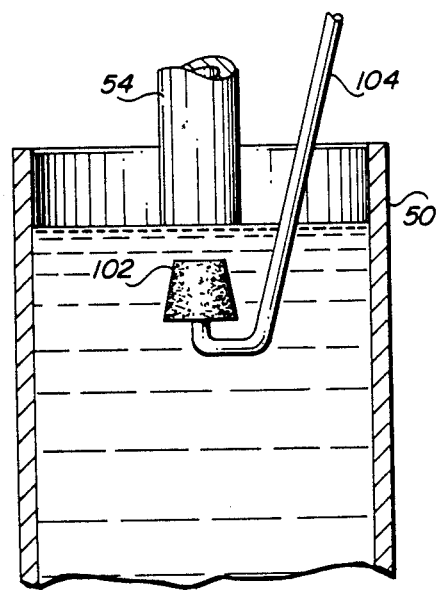
FIG. 6 is an enlarged longitudinal sectional view of the level chamber forming part of the large reservoir, showing means for plugging the input tubing when filling the associated make-up water container.

As best shown in FIG. 4, when the cylinder 12 has been filled to the desired level, the water levels in the level chambers 42 and 50 and in the sight tubes 56 and 58 will be the same. It is then necessary to fill the container 52 and the graduated cylinder 44 with make-up water. This is accomplished in the case of the container 52 by first closing off the bottom of the tube 54 by suitable means such as by the cork assembly shown in FIG. 6, wherein a cork 102 adapted to fit into the open end of the tube 54 is depicted. A rigid handle 104 is attached to the cork which in practice may be a stiff wire which has been bent to shape and adhered to the cork by glue.

With the bottom of the tube 54 closed by the cork the corks or stoppers 80 and 86 are removed and water is introduced through the tubing 78. By filling the container 52 in this manner any air in the container is forced out the tube 82. When the container is filled the corks 80 and 86 are replaced and the cork assembly removed from the end of tube 54.

The graduated cylinder 44 can be filled by using the cork assembly to seal the tube 46 to prevent any water in the cylinder from flowing into the chamber 42 while the cylinder is removed from its support 62. With the stopper 90 remaining in place, the graduated cylinder is inverted, the cork assembly is removed and the cylinder 44 is filled to the desired level. The cork assembly is again inserted to seal the tube 46, the cylinder is repositioned and the cork assembly again removed.

Figure 5A:
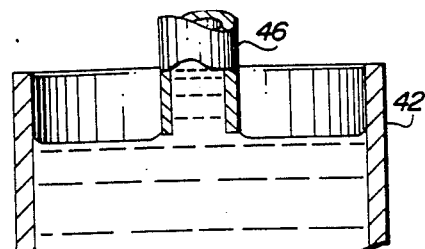
FIG. 5A is an enlarged longitudinal sectional view of the level chamber forming part of the small reservoir, showing the water level at the bottom of the input tube.

In FIG. 4 the water levels in the chambers 50 and 42 are the same, as indicated by the levels of water in the sight tubes 58 and 56. This is the state of the apparatus at the start of the operation of the infiltrometer. The goal is to maintain the water levels in the large and small reservoirs the same, adding enough water to the chambers 42 and 50 in order to make up for losses due to infiltration from the reservoirs into the soil and then measuring the amount of water lost by infiltration from the small reservoir. As shown in FIG. 5A, this initial state is characterized by the bottom end of the tube 46 being sealed off by the surface of the water in the chamber 42.

Figure 5B:
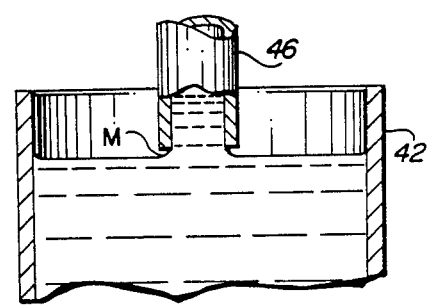
FIG. 5B is a view similar to that of FIG. 5A, but showing the water level after it has been lowered a slight amount due to water from the associated reservoir permeating into the soil.
Figure 5C:
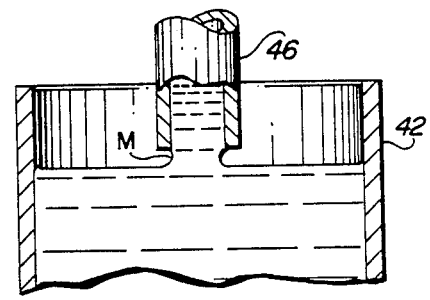
FIG. 5C is a view similar to that of FIG. 5B, but showing the water level after it has been lowered a greater amount.
Figure 5D:
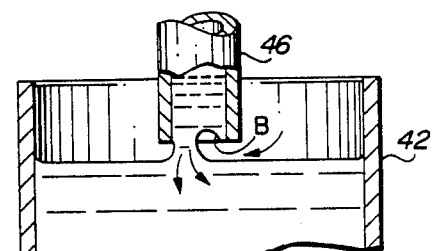
FIG. 5D is a view similar to that of FIG. 5C, but illustrating the phenomenon whereby make-up water enters the chamber to raise the water in the chamber back to its original level.

As shown in FIG. 5B, as the water level drops a meniscus M is formed from the end of the tube 46 to the water level. The volume of water forming the meniscus is supported by the surface tension of the water. As shown in FIG. 5C, as the level of water continues to drop, the meniscus approaches a semicircular shape, necking in so that a cross section of the meniscus would have a smaller area than the cross-sectional area of the inside diameter of the tube 46. Eventually, further lowering of the water level results in a volume of water between the end of the tube 46 and the water level which is greater than the force of the surface tension can maintain. When this occurs the water at the end of the tube flows to one side of the tube as the atmosphere pushes up on the other side, as illustrated at B in FIG. 5D, to form an air bubble. As the air bubble forms, water is displaced from the tube 46 into the chamber 42, the volume of displaced water being equal to the volume of the air bubble after it rises to the top of the container 44. The amount of water transferred by the formation of the first bubble is generally insufficient to raise the water level enough to allow stable conditions to return, resulting in the formation of a series of bubbles until the water level is close enough to the end of the tube 46 so that bubbles can no longer form. When this occurs the system will have returned to a state of equilibrium and the flow of water will stop.

The formation of a bubble in the manner described requires the weight of the water suspended between the end of the tube 46 and the water level in the chamber 42 to cause instability of the surface tension of the suspended water. This in turn requires the inside diameter of the tube 46 to be great enough to ensure that the suspended water meets this minimum weight requirement. It has been found that a minimum inside diameter of 0.5 inches is necessary for the bubble forming process to occur.

The cycle of releasing water from the tube 46 when the water level falls below a certain critical point will be repeated with a frequency depending upon the permeability of the soil. By noting the difference in water level in the graduated cylinder over a period of time, the volume of water taken from the cylinder in order to replace water lost from the small reservoir can readily be determined by reading the markings on the graduated cylinder at the beginning and end of each period.

It will be understood that the level of the large reservoir is maintained at the initial level in the same way. If losses from the large reservoir are large it may be necessary to use a larger make-up water container or to connect two of them in parallel. The size of the graduated cylinder would depend on the rate of loss from the small reservoir. If the water loss is small a small cylinder would be used so that the losses can be accurately read from the markings on the cylinder. In any event, the container 52 as well as the cylinder 44 should be large enough so that all the make-up water is not used over the period between readings.

To render evaporation losses negligible a condensing cover can be installed over the top of the cylinder 12. A simple expedient is to place a sheet of plastic film 106 over the top of the cylinder 12 and tie the edges about the cylinder walls as indicated at 108. By placing a weighted object, such as a smooth rock or sand 110, in the center of the sheet to cause the sheet to take the form of an inverted cone, water vapor condensed on the underside of the sheet will drip back into the large reservoir. A small hole, not shown, in the plastic sheet would be enough to maintain equilibrium atmospheric pressure within the cylinder.

As shown in FIG. 3, a thermometer 112 extending through a stopper 114 in an aperture in the cylinder 12 is provided for the purpose of taking temperature readings of the water. Obviously, the arrangement shown is for illustrative purposes only and may be altered as desired.

As illustrated by the flow arrows in FIG. 3, water in the large reservoir contacting the soil between the concentrically arranged cylinders 12 and 20 will flow down into the compacted fill S and will have a radially outward flow component. Water in the test chamber will flow substantially directly down into the compacted fill and, due to the presence of water in the adjacent soil flowing in from the large reservoir, will not exhibit a tendency to flow outwardly. The boundary effects of flow are thereby effectively eliminated by the device of the invention.

Because the volume of the test chamber is small, the effects of thermal expansion are minimized. Calculations taking into account the difference in the thermal expansion coefficients of water and the steel cylinder 20, and based on a test chamber volume of 100 liters, show that the effective thermal expansion of the chamber amounts to about 6.4 cc per degree Fahrenheit. This is very nearly the same volume as a 1.3 mm change in fluid height within a level chamber of 3.36 square inches cross section. By reading the temperature to an accuracy of $\pm \frac{1}{2}°$ F., a correction factor having an accuracy of $\pm 0.66$ mm can then be added to the measured change in the height of the water column of the small reservoir. The worst case combination of measurement errors would then be only $\pm 1.29\%$, well within the accuracy required of the test. In addition, because the large reservoir has such a large volume, temperature changes in any event are minimized.

It will now be appreciated that the device of the invention is simple to set up and operate in the field, yet it yields measurements which are well within the scope of accuracy required to determine the permeability of the soil layer in question.

It should now be understood that the invention is not necessarily limited to all the specific details described in connection with the preferred embodiment, but that changes to certain features of the preferred embodiment which do not affect the overall basic function and concept of the invention may be made by those skilled in the art without departing from the spirit and scope of the invention, as defined in the appended claims.

What is claimed is:

1. An infiltrometer useful for field testing soil permeability, comprising;
   a large reservoir having an open bottom resting on the soil;
   a small reservoir having an open bottom resting on the soil, the small reservoir being positioned within the large reservoir;
   the small reservoir comprising a relatively large receptacle adjacent the soil and a relatively small receptacle connected thereto and extending upwardly therefrom;
   the volume of the large reservoir greatly exceeding the volume of the small reservoir;
   the ratio of the upper surface area of liquid in the large reservoir to the surface area of the soil covered thereby greatly exceeding the ratio of the upper surface area of liquid in the relatively small receptacle of the small reservoir to the surface area of the soil covered thereby; and
   means for determining the amount of liquid from the small reservoir permeating into the soil.

2. An infiltrometer according to claim 1, wherein the periphery of the small reservoir adjacent the soil is substantially equally spaced from the periphery of the large reservoir.

3. An infiltrometer according to claim 2, wherein the reservoirs are circular in transverse cross section adjacent the soil and are concentrically arranged.

4. An infiltrometer according to claim 1, wherein both the large and the small reservoirs extend upwardly to a height adapted to contain liquid at the same level.

5. An infiltrometer according to claim 4, wherein the height of the relatively large receptacle of the small reservoir is much less than the height of the large reservoir and wherein at least a substantial portion of the overall height of the small reservoir comprises a conduit.

6. An infiltrometer according to claim 1, wherein the means for determining the amount of liquid from the small reservoir permeating into the soil comprises a container containing make-up liquid, the container being in fluid communication with the relatively small receptacle of the small reservoir, and means for automatically introducing make-up liquid from the container into the relatively small receptacle in response to the flow of liquid from the small reservoir into the soil to maintain the liquid level in the small reservoir at a substantially constant height.

7. An infiltrometer according to claim 6, wherein the means for automatically introducing make-up liquid from the container comprises a fluid conduit extending from the container into a chamber, the chamber being part of the relatively small receptacle and containing the upper level of the liquid in the small reservoir, and means causing liquid to flow from the container into the chamber when the level of liquid in the chamber falls sufficiently below the end of the fluid conduit.

8. An infiltrometer according to claim 7, wherein the means causing liquid to flow from the container into the chamber comprises an instability of the surface tension due to the weight of liquid that is suspended between the end of the fluid conduit and the liquid level in the level chamber as the liquid level recedes from the end of the fluid conduit, such instability allowing air to enter the container and displace an equivalent volume of liquid into the small reservoir until the level of the small reservoir rises enough to restore stability of the surface tension and prevent further entrance of air into the container.

9. An infiltrometer according to claim 8, wherein the inside diameter of the fluid conduit between the container and the chamber is of sufficient diameter to ensure instability of the surface tension as the fluid level recedes from the end of the fluid conduit.

10. An infiltrometer according to claim 9, wherein the inside diameter of the fluid conduit between the container and the chamber is at least about 0.5 inch.

11. An infiltrometer according to claim 6, including a second container containing make-up liquid, the second container being in fluid communication with the large reservoir, and means for automatically introducing make-up liquid from the second container into the large reservoir in response to the flow of liquid from the large reservoir into the soil to maintain the liquid level in the large reservoir at a substantially constant height.

12. An infiltrometer according to claim 11, wherein the means for automatically introducing make-up liquid from the second container comprises a fluid conduit extending from the second container into a chamber, the chamber being in fluid connection with the large reservoir and containing liquid corresponding to the upper level of the liquid in the large reservoir, and means causing liquid to flow from the second container into the chamber when the level of liquid in the chamber falls sufficiently below the end of the fluid conduit.

13. An infiltrometer according to claim 12, wherein the means causing liquid to flow from the second container into the chamber comprises an instability of the surface tension due to the weight of liquid that is suspended between the end of the fluid conduit and the liquid level in the level chamber as the liquid level recedes from the end of the fluid conduit, such instability allowing air to enter the second container and displace an equivalent volume of liquid into the small reservoir until the level of the small reservoir rises enough to restore stability of the surface tension and prevent further entrance of air into the second container.

14. An infiltrometer according to claim 13, wherein the diameter of the fluid conduit between the second container and the chamber is of sufficient diameter to ensure instability of the surface tension as the fluid level recedes from the end of the fluid conduit.

15. In a method of determining the permeability of soil, the steps of:
   placing a large reservoir having an open bottom on the soil;
   placing a small reservoir having an open bottom on the soil within the confines of the large reservoir.
   the small reservoir comprising a relatively large receptacle adjacent the soil and a relatively small receptacle connected thereto and extending upwardly therefrom;
   filling the reservoirs with liquid;
   maintaining the liquid levels within the reservoirs.
   the relative sizes of the reservoirs being such that the volume of the large reservoir greatly exceeds the volume of the small reservoir such that thermal expansion and temperature change of liquid in the small reservoir are minimized.
   the ratio of the upper surface area of the liquid in the large reservoir to the surface area of the soil covered thereby greatly exceeds the ratio of the upper surface area of the liquid in the small reservoir to the surface area of the soil covered thereby;
   connecting the liquid in the small reservoir to level gauge means to determine the amount of liquid from the small reservoir permeating into the soil, said level gauge means containing make-up liquid; and
   maintaining fluid communication between the small reservoir, the relatively small receptacle and the level gauge means.

16. A method according to claim 15, wherein the periphery of the small reservoir adjacent the soil is substantially equally spaced from the periphery of the large reservoir.

17. A method according to claim 15, wherein the height of the relatively large receptacle of the small reservoir is much less than the height of the large reservoir.

18. The method according to claim 15 wherein the level gauge means containing the small reservoir make-up fluid is graduated to indicate fluid level and allow a direct reading of the amount of the liquid from the small reservoir permeating the soil.

* * * * *